(12) United States Patent
Matheron et al.

(10) Patent No.: US 9,927,401 B2
(45) Date of Patent: Mar. 27, 2018

(54) GRAVIMETRIC GAS SENSOR HAVING A LOWERED DETECTION LIMIT

(71) Applicants: COMMISSARIAT A L'ENERGIE ATOMIQUE ET AUX ENERGIES ALTERNATIVES, Paris (FR); APIX ANALYTICS, Grenoble (FR)

(72) Inventors: Muriel Matheron, Chambery (FR); Regis Barattin, Grenoble (FR); Vincent Jousseaume, Le Sappey en Chartreuse (FR); Florence Ricoul, Quaix-en-Chartreuse (FR)

(73) Assignees: COMMISSARIAT A L'ENERGIE ATOMIQUE ET AUX ENERGIES ALTERNATIVES, Paris (FR); APIX ANALYTICS, Grenoble (FR)

( * ) Notice: Subject to any disclaimer, the term of this patent is extended or adjusted under 35 U.S.C. 154(b) by 51 days.

(21) Appl. No.: 15/108,428

(22) PCT Filed: Dec. 24, 2014

(86) PCT No.: PCT/EP2014/079301
§ 371 (c)(1),
(2) Date: Jun. 27, 2016

(87) PCT Pub. No.: WO2015/097282
PCT Pub. Date: Jul. 2, 2015

(65) Prior Publication Data
US 2016/0327518 A1     Nov. 10, 2016

(30) Foreign Application Priority Data

Dec. 27, 2013 (FR) ..................................... 13 63628

(51) Int. Cl.
*G01N 29/02* (2006.01)
*G01N 29/036* (2006.01)
(Continued)

(52) U.S. Cl.
CPC ......... *G01N 29/022* (2013.01); *G01N 29/036* (2013.01); *G01N 30/76* (2013.01);
(Continued)

(58) Field of Classification Search
CPC .... G01N 29/022; G01N 29/036; G01N 30/76; G01N 2291/0256
See application file for complete search history.

(56) References Cited

U.S. PATENT DOCUMENTS

| 5,827,947 A | 10/1998 | Miller et al. |
| 2006/0115982 A1* | 6/2006 | Morisue ................ H01L 21/288 438/638 |

(Continued)

FOREIGN PATENT DOCUMENTS

| FR | 2 918 997 A1 | 1/2009 |
| WO | 98/32006 A1 | 7/1998 |

OTHER PUBLICATIONS

J. Arcamone, et al., "VLSI silicon multi-gas analyzer coupling gas chromatography and NEMS detectors," Electron Devices Meeting (IEDM), 2011 IEEE International, Dec. 5, 2011, pp. 29.3.1-29.3.4, XP032096029.

(Continued)

*Primary Examiner* — Hezron E Williams
*Assistant Examiner* — David Z Huang
(74) *Attorney, Agent, or Firm* — Oblon, McClelland, Maier & Neustadt, L.L.P.

(57) ABSTRACT

A gravimetric detector including a nanoelectronic structure including: a fixed part, at least one part suspended from the fixed part, an excitation device to vibrate the suspended part relative to the fixed part, a detector to detect variations in vibration of the suspended part, and a porous functionaliza- (Continued)

tion layer at least partially covering the suspended part, porosity of the functionalization layer being between 3% and 50%.

14 Claims, 6 Drawing Sheets

(51) Int. Cl.
    *G01N 30/76* (2006.01)
    *G01N 30/02* (2006.01)

(52) U.S. Cl.
    CPC . *G01N 2030/025* (2013.01); *G01N 2291/021* (2013.01); *G01N 2291/0256* (2013.01); *G01N 2291/0426* (2013.01); *G01N 2291/0427* (2013.01)

(56) References Cited

U.S. PATENT DOCUMENTS

| | | |
|---|---|---|
| 2009/0155535 A1 | 6/2009 | Jousseaume |
| 2011/0113855 A1 | 5/2011 | Badding et al. |
| 2011/0140235 A1* | 6/2011 | Oda .................. H01L 23/5256 |
| | | 257/529 |

OTHER PUBLICATIONS

S. Fanget, et al., "Gas sensors based on gravimetric detection—A review," Sensors and Actuators B: Chemical, vol. 160, 2011, pp. 804-821.
M. Li, et al., "Nanoelectromechanical Resonator Arrays for Ultrafast, Gas-Phase Chromatographic Chemical Analysis," Nano Letters, vol. 10, 2011, pp. 3899-3903.
S. Guo, et al., "Ellipsometric sensitivity to halothane vapors of hexamethyldisiloxane plasma polymer films," Sensors and Actuators B, vol. 44, 1997, pp. 243-247.
H. Grange, et al., "A New Method for Hermeticity Measurements Using Porous Ultra Low K Dielectrics for SUB-PPM Moisture Detection," Transducers 2009, pp. 168-171.
L Favennec, et al., "Ultralow k using a plasma enhanced chemical vapor deposition porogen approach: Matrix structure and porogen loading influences," Journal of Applied Physics, vol. 102, 2007, 10 pages.
U. Lehmann, et al., "Micro machined gas chromatograph based on a plasma polymerised stationary phase," Micro Total Analysis Systems, 2000, pp. 167-170.
J. Weichart, et al., "Plasma polymerization of silicon organic membranes for gas separation," Surface and Coatings Technology, vol. 59, 1993, pp. 342-344.
International Search Report Issued Apr. 15, 2015 in PCT/EP2014/079301 filed Dec. 24, 2014.
French Search Report dated Aug. 14, 2014 in FR 13 63628 filed Dec. 27, 2014.

* cited by examiner

GRAVIMETRIC GAS SENSOR HAVING A LOWERED DETECTION LIMIT

TECHNICAL DOMAIN AND PRIOR ART

This invention relates to a gravimetric type gas sensor with a lowered detection limit.

Gravimetric type gas sensors comprise gravimetric transducers coated with a chemically active layer the role of which is to capture and concentrate target gases, possibly reversibly and possibly selectively. The transducer converts the adsorbed mass into an electrical signal (frequency variation). Performances of the sensor in terms of resolution and detection limit depend not only on the design of the sensor, for example they depend on geometric parameters, vibration modes, etc., but also the affinity of the active layer towards gases.

The most frequently used gravimetric sensors are quartz crystal microbalances (QCM) coated with organic polymers. The active surface of the QCM is of the order of 0.2 $cm^2$.

There are also gas sensors based on a microelectromechanical structure (MEMS) or nanoelectromechanical structure (NEMS) making use of resonant beams.

Such a gas sensor can be placed at the outlet from a gas phase chromatography column and detect each gas constituent previously separated by the column.

Nanometric dimensions of NEMS result in considerably better sensor performances than are possible with quartz microbalances.

Therefore, an attempt is made to further lower gravimetric sensor detection limits.

PRESENTATION OF THE INVENTION

The purpose of this invention is to make a NEMS type gravimetric detector with a lowered detection limit.

The previously mentioned purpose is achieved by a gravimetric detector comprising a nanoelectromechanical structure comprising at least one suspended part, said suspended part being coated at least partly with a layer of porous material with a porosity of between 3% and 50%, and advantageously between 5% and 40%.

Preferably, the thickness of the porous layer is between 10 nm and 200 nm.

Preferably, the porous material is of the SiOxCyHz or $SiO_w$ type.

Advantageously, the layer of porous material is formed by chemical or physical vapour phase deposition, preventing risks of stiction between the suspended part and the substrate.

Alternately, the layer of porous material is formed by spraying, that is a means of depositing materials such as Graphite and SiOw, where w varies between 0 and 2.

In other words, the gas detector consists of a nanoelectromechanical device comprising a sensitive part functionalised by means of a porous layer that increases the quantity of absorbed compound and lowers the detection limit.

The subject-matter off the presente invention is then a gravimetric detector comprising a nanoelectronic structure comprising a fixed part, at least one part suspended from the fixed part, excitation means to vibrate the suspended part relative to the fixed part, means of detecting variations in vibration of said suspended part, a porous functionalisation layer at least partially covering this suspended part, the porosity of said functionalisation layer being between 3% and 50%.

Preferably, the porosity of the functionalisation layer is between 5% and 40%.

The functionalisation layer is advantageously between 10 nm and 200 nm thick.

The functionalisation layer may be made of a SiOxCyHz type material, where
x is between 1 and 2, preferably between 1.4 and 1.8,
y is between 0.8 and 3, preferably between 1 and 2.5,
z is between 2.5 and 4.5, preferably between 3 and 4.1.

As a variant, the functionalisation layer may be made of a SiOw type material, where w is between 0 and 2.

The functionalisation layer is for example present on at least part of a face of the suspended part opposite the fixed part, advantageously over the entire face of the suspended part opposite the fixed part.

The excitation means are for example electrostatic means, and detection means are for example piezoelectric means.

Another subject-matter of the invention is an analysis assembly comprising a gas phase chromatography column and at least one gravimetric detector according to the invention placed at the outlet from said column.

Another purpose of this invention is a method of manufacturing a gravimetric detector according to the invention, comprising:
manufacturing the nanoelectronic structure;
formation of the functionalisation layer with a porosity of between 3% and 50%, over at least part of the suspended part of the nanoelectronic structure.

The functionalisation layer is obtained for example by chemical vapour phase deposition. A porogenic agent may be used during the chemical vapour phase deposition. The porosity level may be fixed as a function of the porogen flow. The porogenic agent may for example comprise organic molecules, such as norbornadiene, norbornene, alpha terpinene, cyclohexene oxide, cyclopentene oxide, trivertal, etc.

The functionalisation layer may be obtained by adding a precursor and a porogenic agent into a chamber, applying a plasma treatment and then performing a heat treatment to oxidise the porogenic agent.

The functionalisation layer may be formed after the nanoelectronic structure has been released.

BRIEF DESCRIPTION OF THE DRAWINGS

This invention will be better understood after reading the following description and the appended drawings on which.

DETAILED PRESENTATION OF PARTICULAR EMBODIMENTS

For simplification reasons, the nanoelectromechanical structure will be referred to as NEMS in the remainder of the description.

FIG. 1 shows a diagrammatic view of an example embodiment of a gravimetric detector D according to the invention comprising a NEMS with a fixed part 2 and a suspended part 4 that will be vibrated relative to the fixed part. In the example shown, the suspended part 4 is composed of a beam anchored by a longitudinal end 4.1 on the fixed part 2. The detector D also comprises a layer 6 of porous material covering at least the suspended part 4. The porous layer 6 will subsequently be referred to as the "functionalisation layer".

Figure 1A:
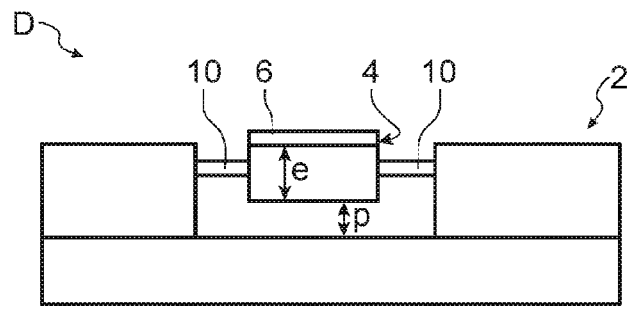
FIG. 1A is a side view shown diagrammatically of an example NEMS that can be used in the detector according to the invention.
Figure 1B:
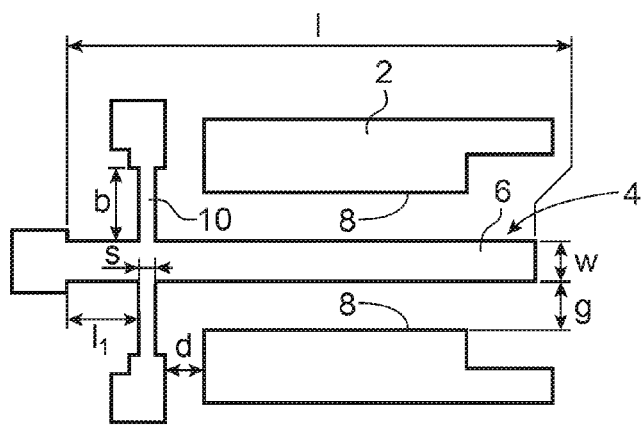
FIG. 1B is a top view of the NEMS in FIG. 1A.

Table T1 below gives two examples of NEMS dimensions, NEMS1 and NEMS2, in µm, the dimensions being given in FIGS. 1A and 1B. $f_0$ is the resonant frequency of the NEMS.

|  | e | p | l | w | S | g | $f_0$ |
|---|---|---|---|---|---|---|---|
| NEMS1 | 0.160 | 0.400 | 5 | 0.3 | 0.08 | 0.2 | 20 |
| NEMS2 | 0.160 | 0.400 | 3.2 | 0.3 | 0.08 | 0.15 | 55 |

The detector also comprises excitation means that will vibrate the suspended part 4 and means of detecting the variation in the vibration frequency of the suspended part due to the adsorbed mass. In the example shown, the excitation means are of the electrostatic type comprising electrodes 8 supported on the fixed part 2 facing the lateral faces of the beam 4.

In the example shown, the detection means are of the piezoresistive type, formed by two piezoresistive gauges 10 connecting the suspended part to the fixed part and deformed by vibrations of the suspended part. Deformation of gauges causes a variation in the electrical resistance measured within each gauge. This variation in the vibration frequency can then be correlated to a given compound. The use of two gauges advantageously provides a differential measurement so that for example this eliminates the influence of variations in external conditions such as temperature variations. As a variant, a single gauge could be used.

In another example, the detection means are of the capacitive type and for example comprise an electrode on the fixed part facing the suspended part, and forming a capacitor with the suspended part for which the capacitance varies with the vibration of the suspended part. Other detection means could be used.

As a variant, the NEMS could comprise several suspended parts. The suspended part may also be a membrane connected to the fixed part 2 by suspension means.

A detector comprising several NEMS is within the scope of this invention.

In the example shown and advantageously, the layer 6 covers the entire upper face of the suspended part 4.

The layer 6 may also fully or partly cover the lower face and fully or partly cover the flanks. The porous layer may also cover the fixed part fully or partly.

The porosity of the porous layer is between 3% and 50%, preferably between 5% and 40%. The inventors have determined that the porosity range [3%; 50%] and preferably [5%; 40%] can give better sensitivity. Preferably the pore radius is between 1 nm and 3 nm, or even between 1 nm and 5 nm. These dimensions have been observed by ellipsoporosimetry, the probe molecule being Toluene, the measurement device being model EP12 made by the SOPRA company.

This percentage represents the volume of pores for a given volume of material.

The thickness of the layer 6 is preferably between 10 nm and 200 nm.

The mass of a functionalisation layer with a thickness of less than 200 nm has a negligible influence on the suspended part. A quantity of compound can be absorbed that is more easily detectable if the porous functionalisation layer is more than 10 nm thick.

According to one preferred example, the porous material is of the SiOCH type. This term denotes a compound with formula SiOxCyHz where:

x is between 1 and 2, preferably between 1.4 and 1.8,
y is between 0.8 and 3, preferably between 1 and 2.5,
z is between 2.5 and 4.5, preferably between 3 and 4.1.

According to another example, the porous material may be of the SiO type. The term denotes a compound with formula SiOw, where w is between 0 and 2. Note that such a compound may be obtained either by spraying or by applying an oxidising plasma on a previously described layer of SiOxCyHz, in order to eliminate Methyl groups. The porous layer is designed to absorb molecules of gas to be detected. The porous material has an open porosity in which pores communicate with each other.

Preferably, the porous layer, and particularly SiOCH, is deposited by vapour phase deposition, particularly a chemical vapour deposition (CVD). The thickness of the SiOxCyHz deposit is then uniform over at least the upper surface of the suspended part.

Alternately, porous materials such as SiO, could be deposited by spraying. This is also the case of porous materials such as Graphite or Alumina.

Making the porous layer from SiOCH or SiO by CVD can very advantageously eliminate risks of stiction that can occur between the suspended part and the fixed part during production of a layer by liquid phase deposition. Capillarity effects due to the use of solvents can cause irreversible bonding of nanostructures. Furthermore, when using a CVD deposition, it is possible to achieve porous layer thicknesses equal to at least 10 nm, which is not the case for a liquid phase deposition.

Furthermore, when using a CVD deposition, it is easy to control the thickness of the deposited material by varying the deposition time.

Furthermore, the SiO and SiOCH layers obtained by CVD deposition have very good thermal stability. This is particularly interesting in the case in which the NEMS are placed at the outlet from a gas phase chromatography column, or even inside a gas phase chromatography column. They may then be exposed to a gas flow at a temperature higher than ambient temperature, for example typically at a temperature of between 40° C. and 300° C. Materials deposited by CVD deposition remain stable at these temperatures, unlike some polymers that can degrade chemically at these temperatures or their mechanical properties can change; for example, melting or crystallisation can occur, causing a significant modification to Young's modulus, that can disturb operation of the NEMS, for which the resonant frequency depends not only on its effective mass but also its stiffness and stresses applied to the resonator.

A NEMS functionalised by means of an SiO or SiOCH layer then has a purely gravimetric response, while in the case of a NEMS functionalised by means of organic polymers, the mechanical properties of deposited layers have a non-negligible influence on the NEMS response.

Layers made of porous SiOCH or porous SiO have good chemical stability, avoiding a drift in the baseline of the sensor.

For example, it has been observed that the dielectric constant of a layer of porous <<low k>> SiOCH deposited by PECVD does not vary over a period of several weeks, which shows good stability in time, particularly with regard to ambient humidity. The term low K refers to materials with low dielectric permittivity, typically less than 2.5.

Finally, since CVD deposition equipment is adapted for deposits on substrates with a diameter of 200 mm or even 300 mm, it is possible to make collective deposits of functionalisation layers for several sensors.

According to one advantageous variant, the deposition may be made by Filament Assisted Enhanced Chemical Vapour Deposition (FACVD) which further improves conformity.

According to another variant, the deposition may be made by chemical vapour phase deposition of a first layer containing SiOCH and the porogenic agent, followed by chemical vapour phase deposition of a second layer so as to form a second layer impermeable to the gas. A foaming step is then carried out, in which pores are formed in the SiOCH layer. The second layer is then eliminated. Such a method is disclosed in patent application FR2918997.

The porous SiOCH layer may be deposited in a known type of PECVD equipment.

The precursors for the matrix are for example organosilicon precursors such as DEMS (diethoxymethylsilane), tetramethyl-cyclotetrasiloxane, dimethyl-dioxiranyl-silane, diethoxy-methyl-oxiranyl-silane, etc.). A plasma is applied to the precursor that is vaporised in the chamber of the PECVD equipment. It fragments by forming radicals that are deposited at least on the surface of the suspended element of the NEMS, and these radicals react together to form a film.

A porogenic agent, for example NBD (Norbornadiene), may advantageously be used to make a porous layer. Alternately, organic molecules for example such as norbornene, alpha terpinene, cyclohexene oxide, cyclopentene oxide, trivertal, etc., may be used.

The plasma treatment is also applied to the porogenic agent, and it then forms inclusions in the layer formed by the precursor. The porogenic agent is eliminated during subsequent annealing leaving pores in the layer, and the matrix is cross-linked.

The duration of the deposit is adjusted to obtain the required thickness.

The deposition is followed by an annealing step that eliminates the porogenic agent and cross-links the matrix. For example, the annealing lasts for a few minutes under UV at 400° C. The annealing duration is adjusted depending on the thickness of the material to be treated.

The porosity level is controlled by controlling the flow of precursors and porogenic agent.

Adding a porogenic agent during the vapour phase deposition controls the porosity and gives low dispersion in the pores of the functionalisation layer.

A porosity of at least 3% may be obtained by using or not using a porogenic agent, the use of a porogenic agent may depend on the values of the various porous layer formation parameters. For example, in the case of a CVD deposition, the porosity may depend on the pressure in the CVD chamber, the temperature of the substrate, the plasma power and/or the precursor flow and/or flows of gases such as oxygen or helium.

The affinity of the layer with toluene will be calculated for SiOCH functionalisation layers with different porosities. The affinity of a material layer with toluene increases as the partition coefficient K of this layer increases.

The affinity of the layer with toluene is characterised by the partition coefficient K defined as K=Δ[toluene in the layer]/ΔC.

It is shown that K=Δf/(SeΔC)

where ΔC is the variation in the gas concentration (in g/cm$^3$).

S is the sensitivity of a quartz microbalance, equal to 2.26×10$^8$ Hz cm$^2$/g e is the layer thickness (in cm).

The values of the partition coefficient K are given in table T2 below.

TABLE T2 values of the partition coefficient K for different values of porosity of an SiOCH layer

| | Porosity | K in the concentration range xx xx ppm |
|---|---|---|
| SiOCH | 27% | 6400 |
| SiOCH | 3% | 1900 |
| SiOCH | 0.6% | 900 |

It is seen that a porous layer according to the invention has a higher partition coefficient than a layer with very low porosity, 0.6% in the case considered.

Consequently, due to this invention, the sensor has good or very good affinity with toluene, in other words it has a good or even very good ability to trap toluene. It could be demonstrated that values of the coefficient K would be similar for other gases such as benzene, ethylbenzene and o-xylene.

Thus, it is considered that the porosity is not sufficient to confer sufficient sensitivity on the material if it is below 3%.

Measurements for detection of aromatic compounds were made on a detector comprising a NEMS with an SiOCH layer deposited as described above, in order to demonstrate the effectiveness of the gas detector comprising a NEMS with a suspended sensitive part provided with a porous functionalisation layer according to the invention.

Figure 2:
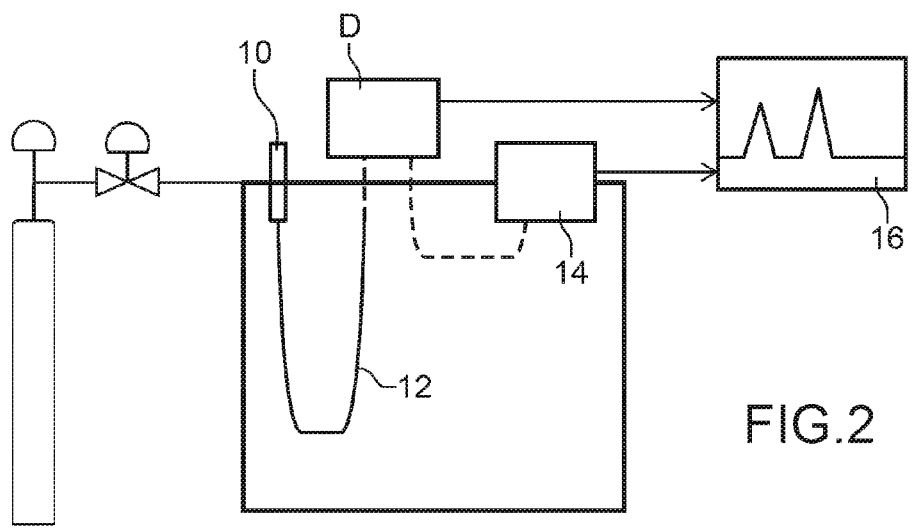
FIG. 2 is a diagrammatic view of the analysis installation making use of at least one detector according to the invention.
Figure 3A:
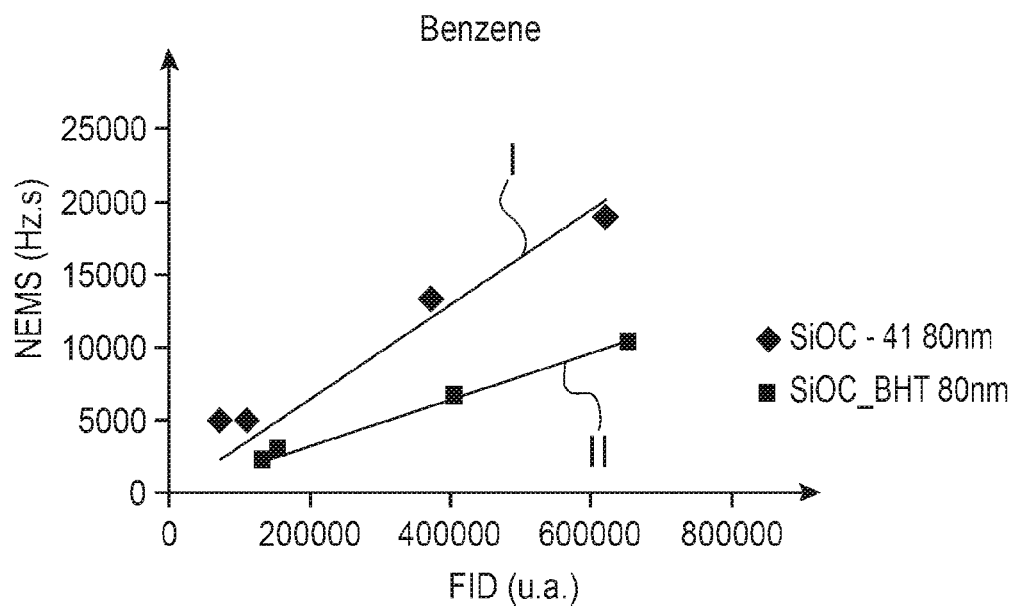
FIGS. 3A to 3D are graphic views of the area of peaks output by the detector according to the invention as a function of the area of peaks output by a FID sensor for two porosities, for benzene, toluene, ethylbenzene and o-Xylene respectively.
Figure 3B:
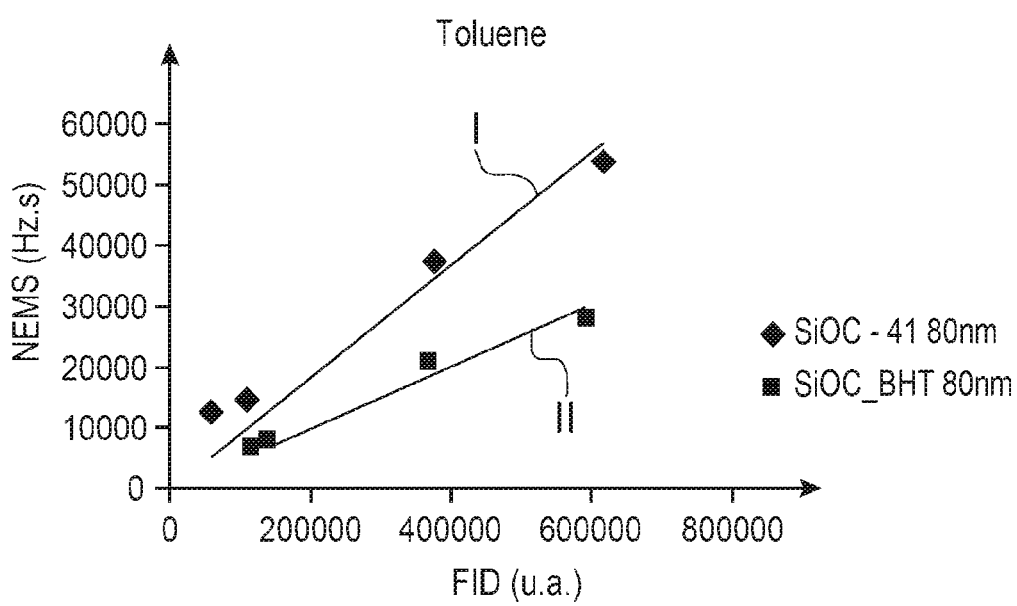
Figure 3C:
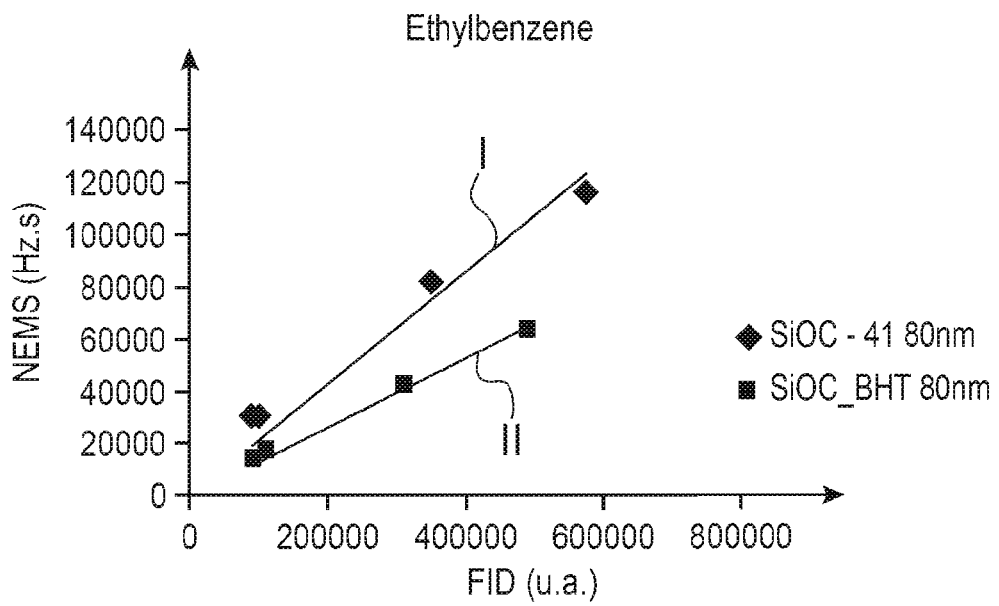
Figure 3D:
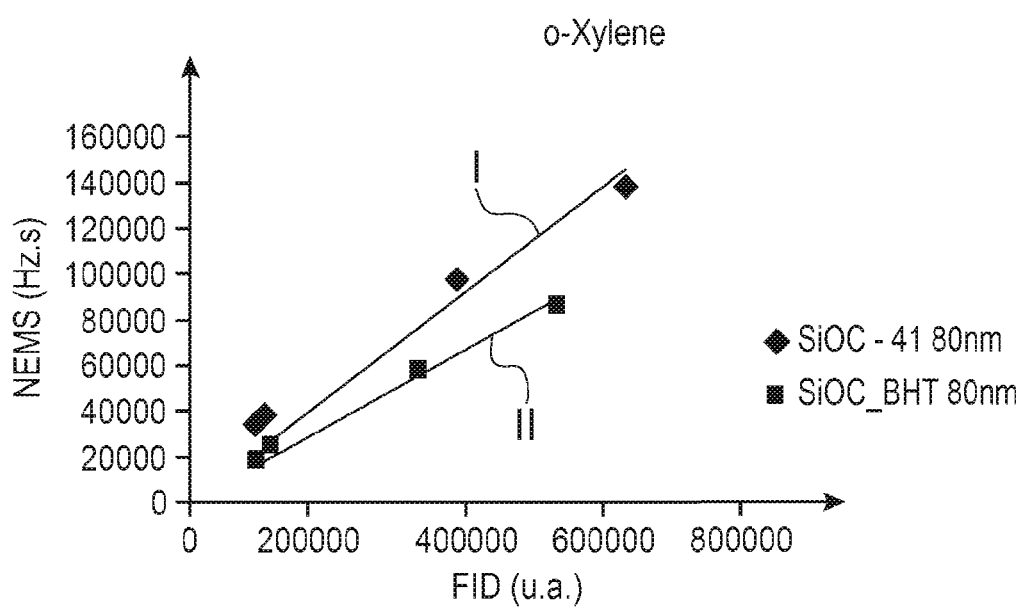

This was done using an installation shown diagrammatically in FIG. 2, comprising an injector 10 for injection of a liquid mix of aromatic compounds; liquid compounds are vaporised in the injector chamber 10 and the vapours thus obtained are injected into the measurement system, a gas phase chromatography column 12 being used to separate each constituent of the injected mix, a NEMS detector D functionalised with an SiOCH layer being located at the outlet from the gas phase chromatography column 12. The NEMS detector D detects each constituent previously separated in the chromatography column 12, and a reference detector 14, in this case a flame ionisation detector (FID) is provided downstream from the NEMS. The FID detector is used to control the quantity of material at the outlet from the column. The detector D and the reference detector 14 are connected to a recorder 16.

Table T3 below shows values of detectable mass in ng corresponding to the detection limit of the functionalised NEMS for two thicknesses (30 nm and 180 nm) of the SiOCH layer with a porosity of 27% and for four compounds: benzene, toluene, ethylbenzene and o-xylene.

TABLE T3 mass detectable by a NEMS detector comprising a functionalisation layer made of SiOC with a porosity of 27%.

|  |  | Detectable mass (ng) |
|---|---|---|
| Unit NEMS SiOC-41-30 nm | Benzene | 5.541 |
|  | Toluene | 3.149 |
|  | Ethylbenzene | 2.357 |
|  | o-Xylene | 2.695 |
| Unit NEMS SiOC-41-180 nm | Benzene | 0.391 |
|  | Toluene | 0.228 |
|  | Ethylbenzene | 0.189 |
|  | o-Xylene | 0.393 |

The detection limit of detectors according to the invention is lower than it is for gas detectors according to the state of the art.

Curves 3A to 3D show the area of peaks obtained by gravimetric measurement made using the NEMS detector in Hz·s as a function of the area of the peak obtained by FID in arbitrary units for 80 nm thick SiOCH layers with a porosity of 27% (curve I) and 3% (curve II). Curve 3A shows detection of benzene, curve 3B shows detection of toluene, curve 3C shows detection of Ethylbenzene, and curve 3D shows detection of o-Xylene.

The area of the peak obtained by FID is proportional to the total mass of detected compound.

The gain in mass absorbed by an SiOCH layer with a porosity of 27% in comparison with an SiOCH layer with a porosity of 3% is 2 for benzene, 1.8 for toluene, 1.6 for ethylbenzene and 1.4 for o-Xylene.

Figure 4A:
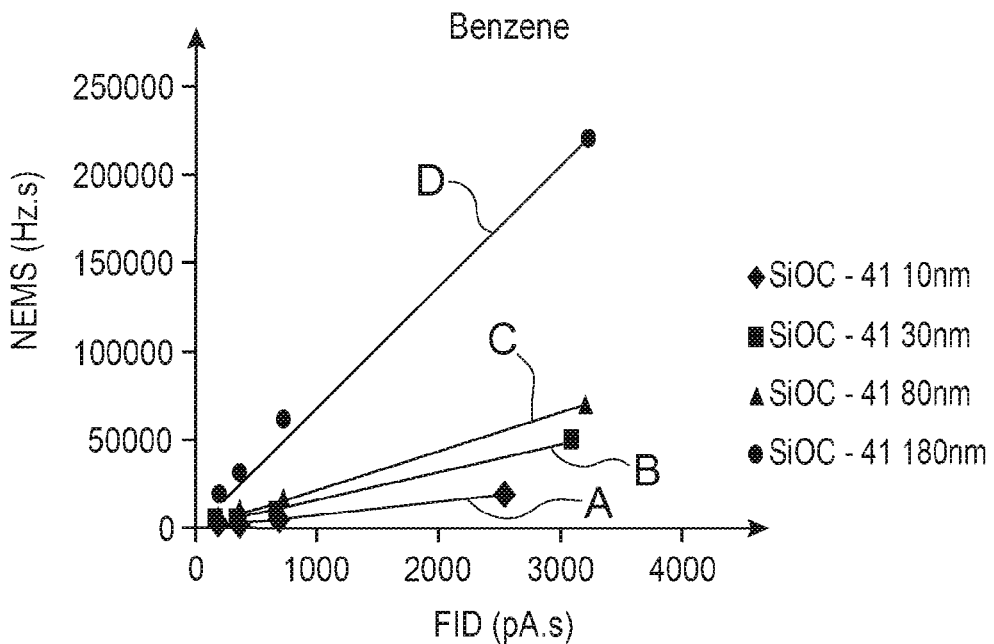
FIGS. 4A to 4D are graphic representations of the area of peaks output by the detector according to the invention as a function of the area of peaks output by a FID sensor for different thicknesses, for benzene, toluene, ethylbenzene and o-Xylene respectively.
Figure 4B:
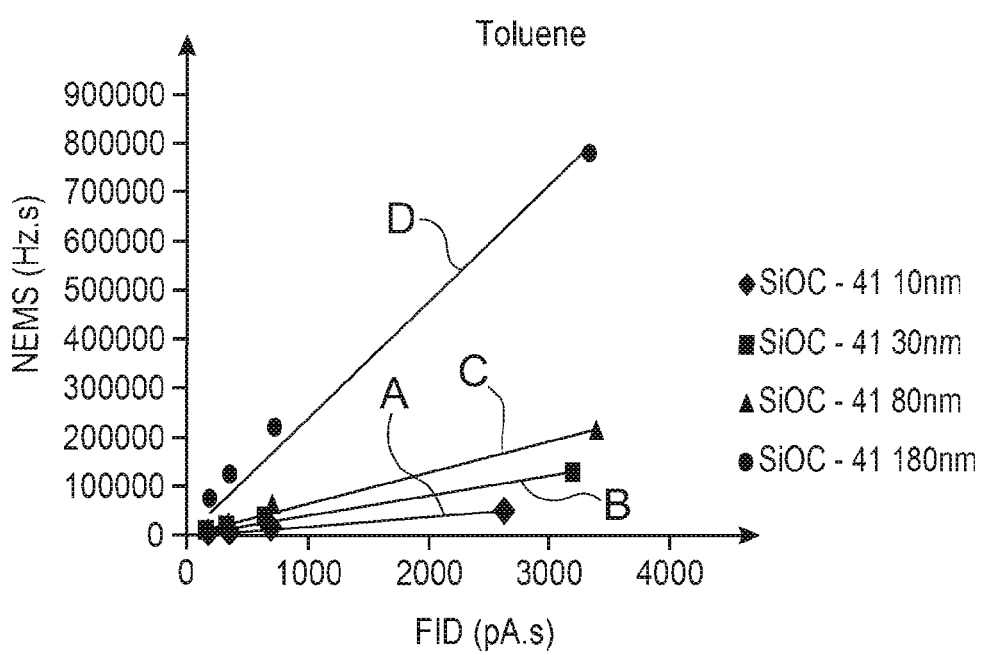
Figure 4C:
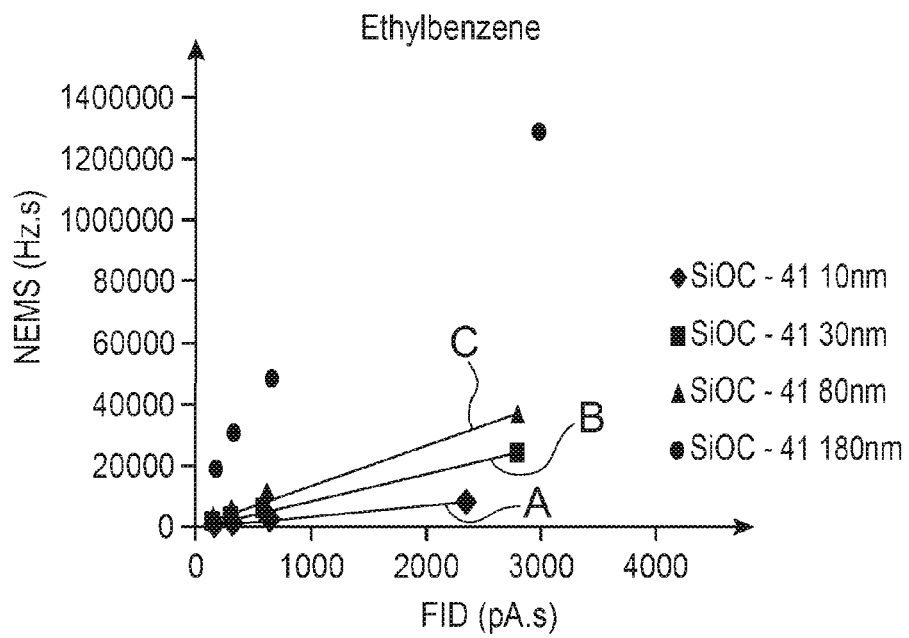
Figure 4D:
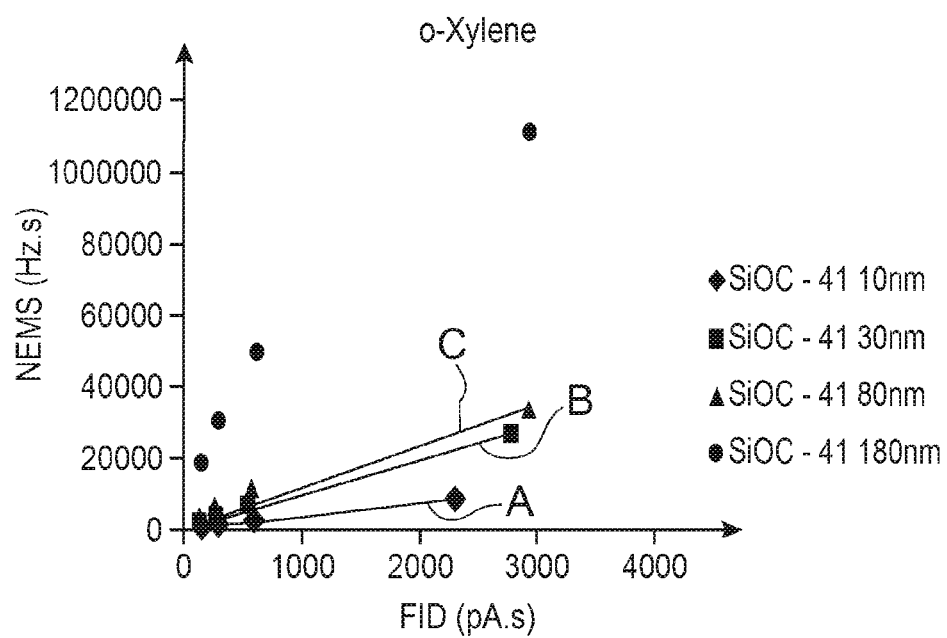

FIGS. 4A and 4B show the area of peaks obtained by gravimetric measurement made using the NEMS in Hz·s as a function of the area of the peak obtained by FID in pA·s (arbitrary units) for SiOCH layers with a porosity of 27% and increasing thickness, namely 10 nm (curve A), 30 nm (curve B), 80 nm (curve C) and 180 nm (curve D). FIG. 4A shows detection of benzene, FIG. 4B shows detection of toluene, FIG. 4C shows detection of Ethylbenzene, and FIG. 4D shows detection of o-Xylene.

Table T4 below shows gains in absorbed mass of toluene calculated between different thicknesses. For example, the first column shows that the gain between a 30 nm layer and a 10 nm layer is equal to 2.

TABLE T4 gain in detected mass as a function of the thickness of the SiOCH layer with 27% porosity

|  | Gain SiOC-41 30 nm/10 nm | Gain SiOC-41 80 nm/30 nm | Gain SiOC-41 180 nm/30 nm |
|---|---|---|---|
| Toluene | ×2 | ×1.6 | ×5.9 |

The partition coefficient of the material of the functionalisation layer relative to toluene is equal to at least 1900. Advantageously, for a thickness of at least 10 nm, the product K×e is equal to at least $1900 \times 10.10^{-7}$ cm = $19 \times 10^{-4}$ cm for toluene.

We will now describe an example embodiment of a manufacturing process of a NEMS detector according to the invention with reference to FIGS. 5A to 5F.

For example, an SOI (Silicon-On-Insulator) substrate is used. It comprises a silicon substrate 102, a dielectric layer 104 for example $SiO_2$ and a layer of monocrystalline silicon 106. For example, the thicknesses of layer 104 and of layer 106 are 400 nm and 160 nm respectively. The layer 106 may be p doped by implantation of boron ions at $1.5 \times 10^{19}$ at./$cm^3$.

The SOI substrate is shown in FIG. 5.

During a subsequent step, the NEMS is made using a lithography step and an etching step on the layer 106.

Advantageously, lithography is a hybrid lithography for example an e-beam and DUV lithography that structures large surfaces with structures with dimensions that can be less than 80 nm, or even 50 nm.

Etching may for example be anisotropic etching.

Figure 5A:
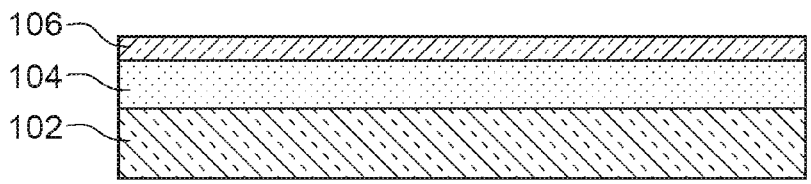
FIGS. 5A to 5F are diagrammatic views of steps for manufacturing a sensor according to one example embodiment of a manufacturing process.
Figure 5B:
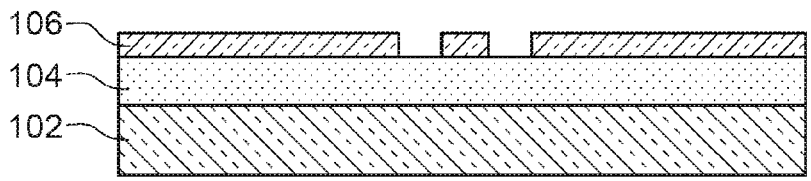

FIG. 5B shows the element thus obtained.

During a subsequent step, a layer 108 of a dielectric, for example $SiO_2$ is formed on the structured layer 106. This layer is then structured by lithography and etching to access the layer 106 in zones 110.

Figure 5C:
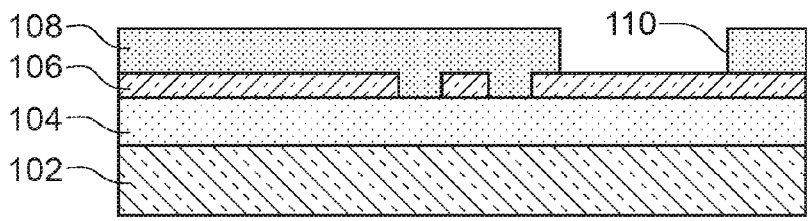

The element thus obtained is shown in FIG. 5C.

During the next step, a layer 114 of conducting material, for example a metal material such as AlSi is formed on the layer 110 in order to form contact pads, and particularly in the zone 110 to access the layer 106. For example, the layer 112 may be 650 nm thick. This layer is then structured thus forming contact pads 114.

Figure 5D:
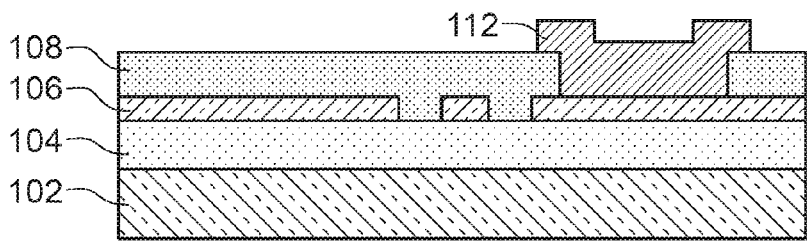

The element thus obtained is shown in FIG. 5D.

During the next step, the NEMS and particularly its suspended part is released, for example by hydrofluoric acid vapour.

Figure 5E:
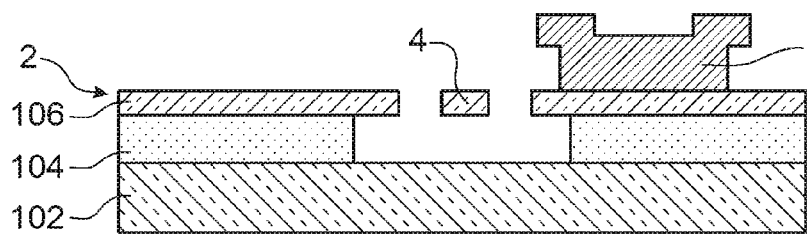

The element thus obtained is shown in FIG. 5E.

A porous functionalisation layer for example made of SiOCH, is then formed during the next step at least on the upper face of the suspended part of the NEMS, preferably by CVD. The thickness of this layer is between 10 nm and 200 nm. This layer is made using the method disclosed above. The functionalisation layer is also deposited on zones adjacent to the suspended part, but only the sensitive part is useful to the sensor.

Figure 5F:
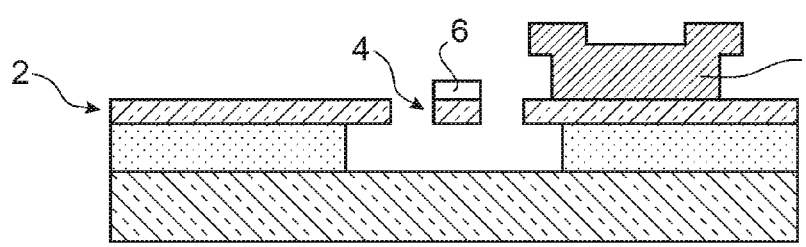

The element thus obtained is shown in FIG. 5F.

Therefore, the invention provides a NEMS type gravimetric sensor with a lowered detection limit. Furthermore, one advantageous manufacturing process can avoid risks of stiction between the suspended part and the fixed part.

The invention claimed is:
1. A gravimetric detector comprising:
   a nanoelectronic structure comprising:
      a fixed part,
      at least one suspended part suspended from the fixed part,
      an excitation device to vibrate the suspended part relative to the fixed part,
      a detector to detect variations in vibration of the suspended part,
      a porous functionalization layer at least partially covering the suspended part,
      wherein the functionalization layer is made of a SiOxCyHz type material,
   wherein
      x is between 1 and 2,
      y is between 0.8 and 3,
      z is between 2.5 and 4.5, and
         wherein porosity of the functionalization layer is between 3% and 50%.
2. The gravimetric detector according to claim 1, wherein the porosity of the functionalization layer is between 5% and 40%.

3. The gravimetric detector according to claim 1, wherein thickness of the functionalization layer is between 10 nm and 200 nm.

4. A gravimetric detector according to claim 1, wherein the functionalization layer is present on at least part of a face of the suspended part opposite the fixed part, or over an entire face of the suspended part opposite the fixed part.

5. A gravimetric detector according to claim 1, wherein the excitation device is an electrostatic device.

6. A gravimetric detector according to claim 1, wherein the detector is a piezoelectric device.

7. A method of manufacturing a gravimetric detector according to claim 1, comprising:
manufacturing the nanoelectronic structure;
forming the functionalization layer with a porosity of between 3% and 50%, over at least part of the suspended part of the nanoelectronic structure.

8. A manufacturing method according to claim 7, wherein the functionalization layer is obtained by chemical vapor phase deposition.

9. A manufacturing method according to claim 8, wherein a porogenic agent is used during the chemical vapour phase deposition.

10. A manufacturing method according to claim 9, wherein the porosity is fixed as a function of the porogen agent flow.

11. A manufacturing method according to claim 9, wherein the porogenic agent comprises organic molecules, or norbornadiene, norbornene, alpha terpinene, cyclohexene oxide, cyclopentene oxide, trivertal.

12. A manufacturing method according to claim 7, wherein the functionalization layer is obtained by adding a precursor and a porogenic agent into a chamber, applying a plasma treatment, and then performing a heat treatment to oxidize the porogenic agent.

13. A manufacturing method according to claim 7, wherein the functionalization layer is formed after the nanoelectronic structure has been released.

14. An analysis assembly comprising:
one gas phase chromatography column and at least one gravimetric detector placed at an outlet from the gas phase chromatography column, and wherein the gravimetric detector comprises a nanoelectronic structure comprising:
a fixed part,
at least one suspended part suspended from the fixed part,
an excitation device to vibrate the suspended part relative to the fixed part,
a detector to detect variations in vibration of the suspended part,
a porous functionalization layer at least partially covering the suspended part,
the functionalization layer being made of a SiOxCyHz type material, wherein
x is between 1 and 2,
y is between 0.8 and 3,
z is between 2,5 and 4,5, and
porosity of the functionalization layer being between 3% and 50%.

* * * * *